United States Patent [19]

Nasuno et al.

[11] Patent Number: 5,506,194
[45] Date of Patent: Apr. 9, 1996

[54] PYRAZOLE DERIVATIVES AND HERBICIDAL COMPOSITIONS

[75] Inventors: Ichiro Nasuno; Mitsuru Shibata; Masashi Sakamoto; Kazuyoshi Koike, all of Sodegaura, Japan

[73] Assignee: Idemitsu Kosan Co., Ltd., Tokyo, Japan

[21] Appl. No.: 367,183

[22] PCT Filed: Jun. 25, 1993

[86] PCT No.: PCT/JP93/00867

§ 371 Date: Dec. 27, 1994

§ 102(e) Date: Dec. 27, 1994

[87] PCT Pub. No.: WO94/01431

PCT Pub. Date: Jan. 20, 1994

[30] Foreign Application Priority Data

Jul. 13, 1992 [JP] Japan ..................... 4-185526

[51] Int. Cl.$^6$ .................... A01N 43/56; C07D 409/02
[52] U.S. Cl. ......................... 504/282; 548/365.7
[58] Field of Search ............... 548/365.7; 504/282

[56] References Cited

FOREIGN PATENT DOCUMENTS 2173 1/1990 Japan.

Primary Examiner—Robert W. Ramsuer
Attorney, Agent, or Firm—Frishauf, Holtz, Goodman, Langer & Chick

[57] ABSTRACT

Pyrazole derivatives of the formula,

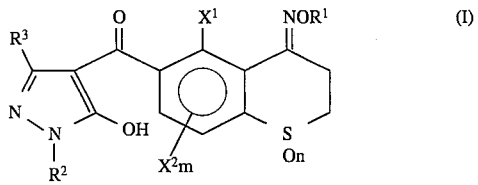

(wherein $R^1$ is a $C_1$–$C_6$ alkyl group, each of $R^2$, $X^1$ and $X^2$ is independently a C1–C4 alkyl group, $R^3$ is hydrogen or a $C_1$–$C_4$ alkyl group, m is an integer of 0 or 1, and n is an integer of 0, 1 or 2.) or salts thereof have high selectivity to corn, wheat and barley and can control grasses and broad-leaved weeds by any treatment of foliar treatment and soil treatment at a low dosage.

21 Claims, No Drawings

PYRAZOLE DERIVATIVES AND HERBICIDAL COMPOSITIONS

This application is a 371 of PCT/JP93/00867 filed Jun. 25, 1993.

TECHNICAL FIELD

The present invention relates to pyrazole derivatives, a herbicide containing the pyrazole derivative(s) as an active ingredient, and novel intermediate compounds useful for the production of the pyrazole derivatives.

TECHNICAL BACKGROUND

During a growing period of corn, etc., a triazine-based herbicide such as atrazine and acid anilide-based herbicides such as alachlor and metolachlor have been conventionally used. However, atrazine shows low efficacy to gramineous weeds, and alachlor and metolachlor show low efficacy to broad-leaved weeds. It is therefore difficult at present to control gramineous weeds and broad-leaved weeds together with a single herbicide. Further, the above herbicides are undesirable in view of an environmental problem due to their high dosage requirement.

On the other hand, it is known that specific 4-benzoyl-pyrazole derivatives have herbicidal activity (see JP-A-63-122672, JP-A-63-122673. JP-A-63-170365, JP-A-1 -52759, JP-A-2-173 and JP-A-2-288866).

Further, for example, pyrazolate of the following formula is known as a commercial herbicide.

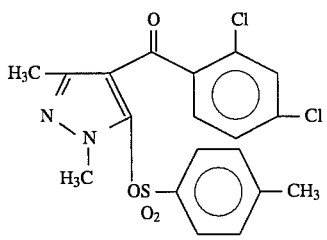

However, pyrazole derivatives having a thiochroman ring such as compounds of the present invention to be specified later are not known yet, and derivatives having an alkoxyimino group are not known, either.

Meanwhile, the commercially available pyrazolate is a herbicide for use in a paddy field., and it hardly has herbicidal activity when used in a plowed field. Further, in foliar treatment, the 4-benzoyl-pyrazole derivatives that have been already disclosed have activity to broad-leaved weeds such as cocklebur, velvetleaf, slender amaranth, etc., in a plowed field, while their activity is practically insufficient. Further, they show very poor activity to grasses such as green foxtail, fingergrass, barnyardgrass, etc. In soil treatment, the above derivatives show very poor activity to grasses such as green foxtail, crabgrass, barnyardgrass, etc, and to broad-leaved weeds such as cocklebur, velvetleaf, slender amaranth, etc.

DISCLOSURE OF THE INVENTION

It is a first object of the present invention to provide a novel pyrazole derivative which shows high selectivity to corn, wheat and barley and which can control grasses and broad-leaved weeds at low dosage by any one of Foliar treatment and soil treatment.

It is a second object of the present invention to provide a herbicide containing the above pyrazole derivative as an active ingredient.

It is a third object of the present invention to provide a novel intermediate compound useful for the production of the above novel pyrazole derivative.

The above first object is achieved by a pyrazole derivative of the formula,

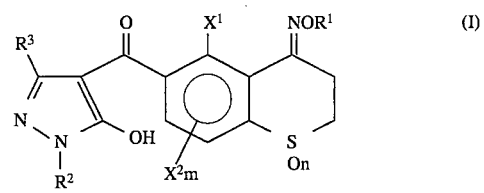

(wherein $R^1$ is a $C_1-C_6$ alkyl group, each of $R^2$, $X^1$ and $X^2$ is independently a $C_1-C_4$ alkyl group, $R^3$ is hydrogen or a $C_1-C_4$ alkyl group, m is an integer of 0 or 1, and n is an integer of 0, 1 or 2.) or a salt thereof.

The above second object is achieved by a herbicide containing the pyrazole derivative of the above formula (I) and/or a salt thereof as active ingredient.

Further, the above third object is achieved by an aromatic carboxylic acid derivative of the formula,

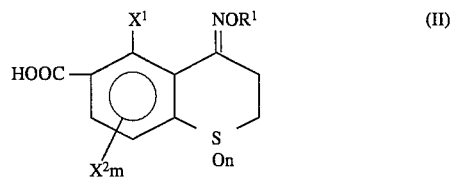

(wherein $R^1$ is a $C_1-C_6$ alkyl group, each of $X^1$ and $X^2$ is independently a $C_1-C_4$ alkyl group, m is an integer of 0 or 1, and n is an integer of 0, 1 or 2), or a salt thereof.

PREFERRED EMBODIMENTS FOR WORKING THE INVENTION

First, the novel pyrazole derivative of the present invention will be explained.

The novel pyrazole derivative of the present invention includes compounds of the formula (I).

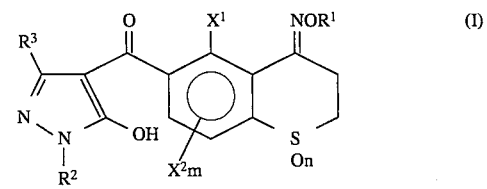

In the formula (i), $R^1$ is a $C_1-C_6$ alkyl group such as methyl., ethyl, propyl, butyl, pentyl or hexyl, and each of $R^2$, $X^1$ and $X^2$ is independently a $C_1-C_4$ alkyl group such as methyl, ethyl, propyl such as n-propyl or i-propyl or butyl such as n-butyl. The propyl, butyl, pentyl and hexyl may be linear or branched as described above. $R^1$ is preferably a $C_1-C_4$ alkyl group, more preferably methyl, ethyl or i-propyl.

Each of $R^2$, $X^1$ and $X^2$ is independently a $C_1-C_4$ alkyl group, and the $C_1-C_4$ alkyl includes methyl, ethyl, propyl such as n-propyl or i-propyl and butyl such as n-butyl. The propyl and butyl may be linear or branched as described above. Preferred is methyl or ethyl.

$R^3$ is hydrogen or a $C_1-C_4$ alkyl group, and the $C_1-C_4$ alkyl group includes those specified regarding the above $R^2$, $X^1$ and $X^2$. Preferred is hydrogen or methyl and more preferred is hydrogen. The propyl and butyl may be linear or branched.

m represents the number of $X^2$, and m is an integer of 0 or 1. When m is 1, the site where $X^2$ is substituted is preferably the 8-position.

n represents the number of oxygen atom(s), and n is an integer of 0, 1 or 2. That is, when n is 0, sulfide is represented, when n is 1, sulfoxide is represented, and when n is 2, sulfone is represented. Preferred is n=2, i.e., sulfone.

The pyrazole derivative of the formula (I) can have the following three structures due to its tautomerism. The pyrazole derivative of the present invention may be a compound having any one of these structures or may be a mixture of compounds having these structures.

Further, the pyrazole derivative of the formula (I) is an acidic substance, and can be easily converted to a salt by treatment with a base. The salt is also included in the pyrazole derivative of the present invention.

The above base is selected from known bases without any limitation, and examples thereof include organic bases such as amines and anilines and inorganic bases such as sodium compounds and potassium compounds. The amines include monoalkylamine, dialkylamine and trialkylamine. The alkyl group in the alkylamines is generally a $C_1$-$C_4$ alkyl group. The anilines include aniline, monoalkylaniline and dialkylaniline. The alkyl group in the alkylanilines is generally a $C_1$-$C_4$ alkyl group. The sodium compounds include sodium hydroxide and sodium carbonate. The potassium compounds include potassium hydroxide and potassium carbonate.

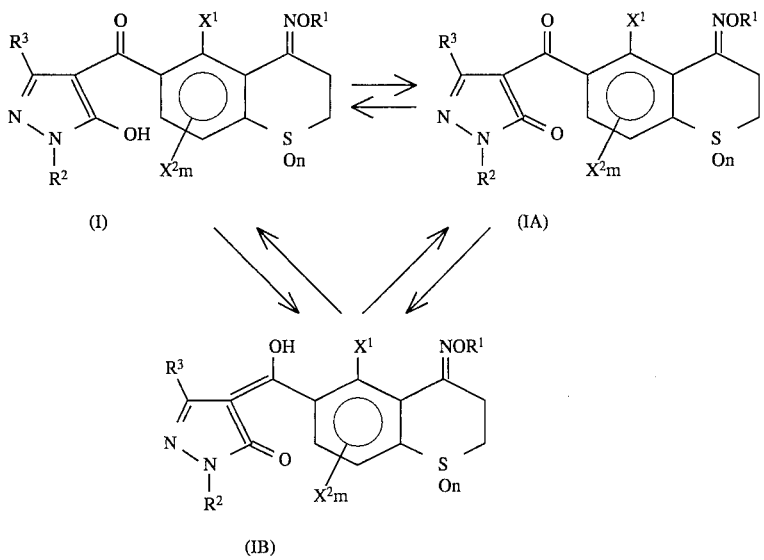

Further, the pyrazole derivative of the formula (I) includes geometrical isomers with regard to an alkoxyimino group as follows. The pyrazole derivative of the present invention may be any one of the following isomers, or may be a mixture of the isomers. When m is 1, the substituent $X^2$ can bond to the 7-position or the 8-position, while $X^2$ preferably bonds to the 8-position.

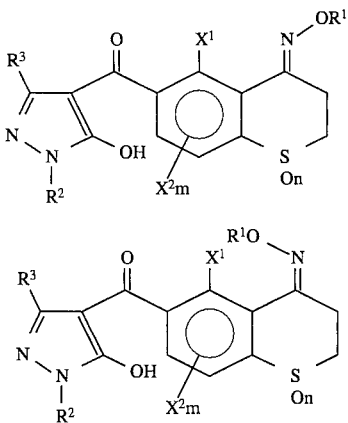

The herbicide of the present invention contains the novel pyrazole derivative of the formula (I) and/or a salt thereof as active ingredient. These compounds may be used as follows. The pyrazole derivative and/or the salt thereof are/is mixed with a liquid carrier such as a solvent or a solid carrier such as a fine mineral powder, and the mixture is prepared into the form of a wettable powder, an emulsion, a dust or granules. For imparting these compounds with emulsifiability, dispersibitity and wettability in producing the above preparations, a surfactant can be added.

Where the herbicide of the present invention is used in the form of a wettable powder, a composition is prepared by mixing 10 to 55% by weight of the pyrazole derivative of the present invention or the salt thereof, 40 to 88% by weight of a solid carrier and 2 to 5% by weight of a surfactant, and the resultant composition may be used. When it is used in th form of an emulsion, the emulsion can be prepared by mixing 20 to 50% by weight of the pyrazole derivative of the present invention or the salt thereof, 35 to 75% by weight of a solvent and 5 to 15% by weight of a surfactant.

On the other hand, when the herbicide of the present invention is used in the form of dust, the dust can be prepared by mixing 1 to 15% by weight of the pyrazole derivative of the present invention or the salt thereof, 80 to 97% by weight of a solid carrier and 2 to 5% by weight of a surfactant. Further, when it is used in the form of granules, the granules can be prepared by mixing 1 to 15% by weight of the pyrazole derivative of the present invention and/or the salt thereof, 80 to 97% by weight of a solid carrier and 2 to 5% by weight of a surfactant. This solid carrier is selected from fine mineral powders, and examples of these fine mineral powders include diatomaceous earth, oxides such as slaked lime, phosphates such as apatite, sulfates such as gypsum, and silicates such as talc, pyrophyllite, clay, kaolin, bentonite, acid clay, white carbon, powdered quartz and a silica powder.

The above solvent is selected from organic solvents, and specific examples of the organic solvents include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl fumarate, amides such as dimethylformamide, and mixtures of these.

Further, the above surfactant is selected from anionic surfactants, nonionic surfactants, cationic surfactants and amphoteric surfactants (amino acid and betaine).

The herbicide of the present invention may contain other herbicidally active component as required in combination with the pyrazole derivative of the formula (I) and/or the salt thereof as an active ingredient. This "other" herbicidally active component includes known herbicides such as phenoxy, diphenylether, triazine, urea, carbamate, thiolcarbamate, acid anilide, pyrazole, phosphoric acid, sulfonylurea and oxadiazon herbicides. This "other" herbicide is properly selected from these herbicides.

Further, the herbicide of the present invention may be used in combination with an insecticide, a fungicide, a plant growth regulator and a fertilizer as required.

The novel pyrazole derivative of the present invention can be produced by the following method (A) or (B).

Method (A)

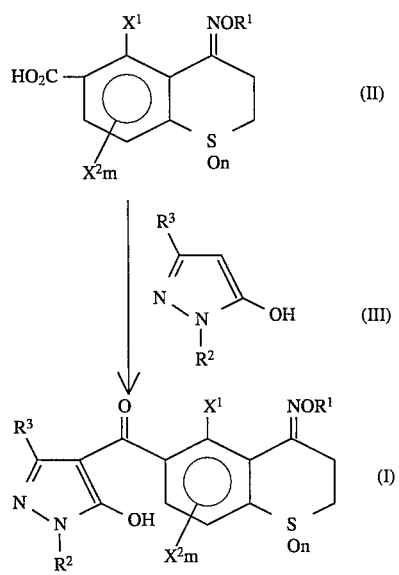

The compound of the formula (II) and the compound or the formula (III) are allowed to react in an inert solvent in the presence of a dehydrating agent such as N,N'-dicyclohexylcarbodiimide (to be abbreviated as DCC hereinafter) and a base to produce the pyrazole derivative of the formula (I).

In the above method (A), the compound of the formula (III) is preferably used in an amount of 1.0 to 3.0 per mole of the compound of the formula (II). The molar amount of DCC is preferably 1.0 to 1.5 times as large as the molar amount of the compound of the formula (II). The base used together with DCC is not specially limited, while potassium carbonate, sodium carbonate, or the like is preferably used in an amount of 0.5 to 2.0 mol per mole of the above compound of the formula (II). The inert solvent is not specially limited if it is inert to the reaction, while t-butyl alcohol, t-amyl alcohol and i-propyl alcohol are preferred. The reaction temperature can be set in the range of from room temperature to the boiling point of the solvent, while it is preferably 50° to 100° C.

The pyrazole compound of the formula (III) used as a reaction reagent in the above method (A) can be synthesized, for example, by the method described in JP-A- 61-257974.

The aromatic carboxylic acid derivative of the Formula (II),

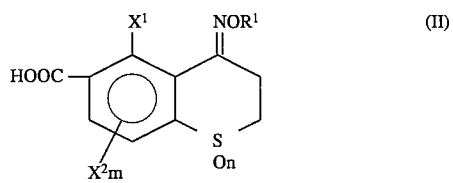

(wherein $R^1$ is a $C_1$–$C_6$ alkyl group, each of $X^1$ and $X^2$ is independently a $C_1$–$C_4$ alkyl group, m is an integer of 0 or 1, and n is an integer of 0, 1 or 2), which is used for the reaction with the compound of the formula (III), is a novel compound described in no literature and useful as an intermediate compound for the production of the pyrazole derivative of the present invention.

The aromatic carboxylic acid derivative of the formula (II) includes geometrical isomers with regard to an alkoxyimino group as follows. The aromatic carboxylic acid derivative of the present invention may be any one of the following isomers or may be a mixture of these isomers. When m is 1, the substituent $X^2$ can bond to any one of the 7-position and 8-position, while it preferably bonds to the 8-position.

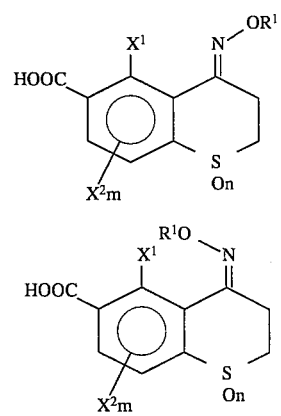

Further, the aromatic carboxylic acid derivative of the formula (II) is an acidic substance, and can be easily converted to a salt by treating it with a base. This salt is also included in the aromatic carboxylic acid derivative of the present invention.

The above base is selected from known bases without any limitation, and examples thereof include organic bases such as amines and anilines and inorganic bases such as sodium compounds and potassium compounds. The amines include monoalkylamine, dialkylamine and trialkylamine. The alkyl group in the alkylamines is generally a $C_1$–$C_4$ alkyl group. The anilines include aniline, monoalkylaniline and dialkylaniline. The alkyl group in the alkylanilines is generally a $C_1$–$C_4$ alkyl group. The sodium compounds include sodium hydroxide and sodium carbonate. The potassium compounds include potassium hydroxide and potassium carbonate.

As described above, the aromatic carboxylic acid derivative of the formula (II) includes sulfide (n=0), sulfoxide (n=1) and sulfone (n=2). These compounds are produced by the following means (x) and (y).

Means (x): Method of sulfide synthesis

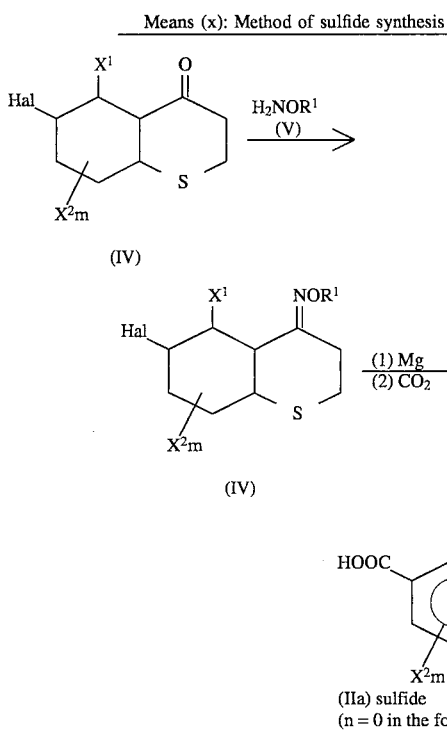

In the above formulas (IV) and (VI), Hal shows halogen such as chlorine, bromine and so on.

The thiochroman-4-one of the formula (IV) used as a starting material can be produced by a variety of methods such as the methods described in JP-A-58-198483, International Patent, Publication WO88/06155 and Canadian Journal of Chemistry (CAN. J. CHEM.), vol. 51, page 839 (1973).

The synthesis of an oxime (IV) from a ketone (IV) is carried out by reacting the ketone (IV) and an alkoxyamine (V) in water or in an organic solvent (e.g., ethanol, methanol or acetic acid) in the presence of an acid catalyst (e.g., hydrochloric acid) or a basic catalyst e.g., pyridine, aniline, sodium hydroxide or sodium carbonate) at a temperature between 0° C. and the reflux temperature of the solvent (water or organic solvent). In one preferred example, the reaction is carried out in ethanol in the presence of pyridine at the reflux temperature. In this reaction, the amount of the alkoxyamine (V) per mole of the ketone (IV) is preferably 1.0 to 5.0 mol, particularly preferably 1.0 to 2.0 mol.

Then the above-obtained oxime (VI) is converted to a Grignard reagent by reacting it with magnesium (Mg), and then carbon dioxide ($CO_2$) is reacted with the Grignard reagent to obtain a sulfide (IIa) (n=0 in the formula (II)) included in the aromatic carboxylic acid derivative of the formula (II). It is preferred to use ethers such as diethyl ether and tetrahydrofuran as a solvent. The reaction temperature is preferably –78° to 50° C, particularly preferably 0° to 50° C.

The molar amount of magnesium (Mg) used for obtaining the Grignard reagent is preferably 1.0 to 5.0 times as large as the molar amount of the oxime (VI). This reaction for forming the Grignard reagent is preferably carried out in the co-presence of alkyl iodide such as methyl iodide or alkyl bromide such as ethyl bromide, since this reaction proceeds smoothly. The molar amount of the alkyl halide used in this case is preferably 0.1 to 3.0 times as large as the molar amount of the oxime (VI).

The reaction between the Grignard reagent and carbon dioxide ($CO_2$) is carried out by bubbling carbon dioxide gas from a bomb into the Grignard reagent in the solvent or by bubbling carbon dioxide gas generated from dry ice (solid carbondioxide) into the Grignard reagent in the solvent. Further, dry ice may be directly added to the Grignard reagent for the reaction.

Means (y): Syntheses of sulfoxide and sulfone

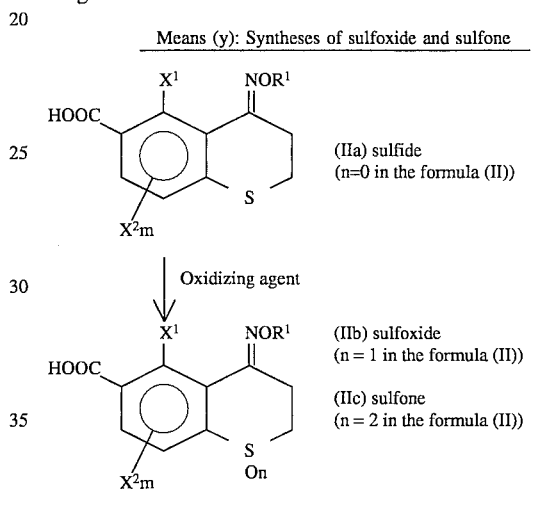

An oxidizing agent (e.g., hydrogen peroxide, peracetic acid or sodium metaperiodate) is allowed to react with the sulfide (IIa), obtained by the above means (x), in a solvent (e.g., acetic acid, water or methanol) to obtain a sulfoxide (IIb) or a sulfone (IIc). When the oxidizing agent is allowed to react in an amount of 1 mole equivalent to the sulfide (IIa), the sulfoxide (IIb) is obtained. When the oxidizing agent is allowed to react in an amount of 2 mole equivalent to the sulfide (IIa), the sulfone (IIc) is obtained.

The process for the production of the novel pyrazole derivative of the formula (I), provided by the present invention, will be again explained hereinafter. The novel pyrazole derivative can be obtained by the following method (B) in addition to the method (A).

Method (B)

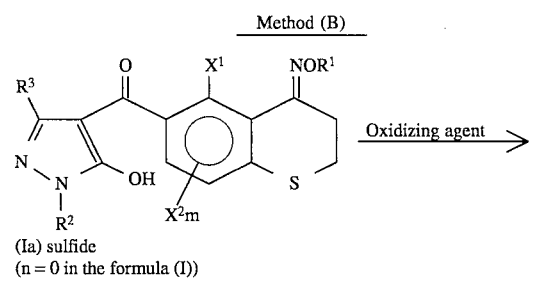

-continued
Method (B)

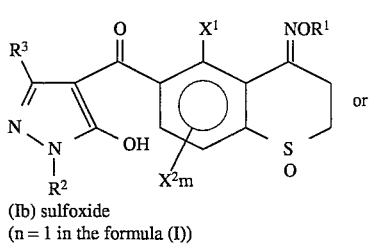
(Ib) sulfoxide
(n = 1 in the formula (I))

or

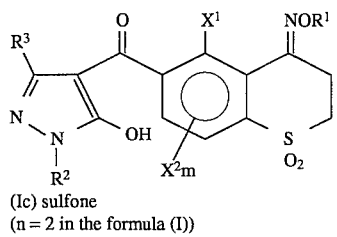
(Ic) sulfone
(n = 2 in the formula (I))

An oxidizing agent (e.g., hydrogen peroxide, peracetic acid or sodium metaperiodate) is allowed to react with the sulfide of the formula (Ia) in a solvent (e.g., acetic acid, water or methanol) to obtain the sulfoxide of the formula (Ib) (n=1 in the formula (I)) included in the pyrazole derivative (I) of the present invention or the sulfone of the formula (Ic) (n=2 in the formula (I)) included in the pyrazole derivative (I) of the present invention. When the oxidizing agent is allowed to react in an amount of 1 mole equivalent to the sulfide (Ia), the sulfoxide (Ib) is obtained, and when it is allowed to react in an amount of 2 mole equivalent to the sulfide (Ia), the sulfone (Ic) is obtained.

The sulfide of the formula (Ia) used as a starting material in the method (B) is included in the pyrazole derivative of the present invention, and it can be obtained by the following reaction.

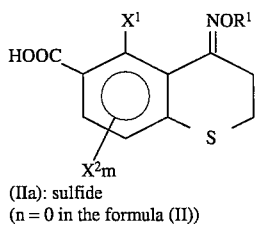
(IIa): sulfide
(n = 0 in the formula (II))

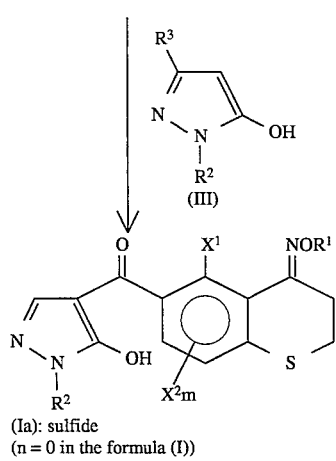
(Ia): sulfide
(n = 0 in the formula (I))

Concerning the method of synthesizing the compound (Ia) by the reaction between the compound (IIa) and the compound (III), see the explanation given in the above method (A).

The present invention will be further explained hereinafter by reference to Examples. However, the present invention shall not be limited by these Examples.

PREPARATION EXAMPLES OF AROMATIC CARBOXYLIC ACID DERIVATIVE AS INTERMEDIATE COMPOUND

Preparation Example 1

A reaction scheme is first shown for facile understanding of the subject reaction.

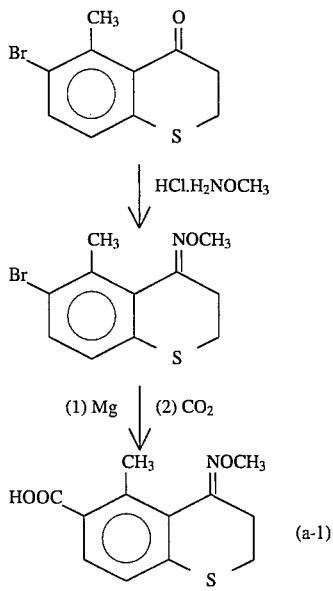

(1) 3.0 Grams (12 mmol) of 5-methyl-6-bromothiochroman-4-one and 1.9 g (23 mmol) of O-methylhydroxylamine hydrochloride were refluxed under heat in a mixed solvent containing 10 ml of ethanol and 10 ml of pyridine for 30 minutes. The solvents were distilled off under reduced pressure, and then 50 ml of 5% hydrochloric acid was added to form a solid. The solid was recovered by filtration, washed with water and dried to give 3.2 g of 4-methoxyimino-5-methyl-6-bromothiochroman (yield 93%).

(2) 1.1 Grams (46 mmol) of magnesium was dispersed in 10 ml of THF, and 2.2 g (20 mmol) of ethyl bromide was added dropwise under nitrogen. The resultant mixture was allowed to react for 10 minutes, and then a solution of 2.9 g (10 mmol) of the 4-methoxyimino-5-methyl-6-bromothiochroman obtained in the above (1) in THF was gradually added at room temperature. The mixture was refluxed for 3 hours and then cooled to room temperature, and carbon dioxide gas was bubbled for 1 hour. 5% Hydrochloric acid was added to the reaction mixture, and the reaction mixture was extracted with ether. The ether layer was extracted with 5% aqueous potassium carbonate, and the aqueous layer was neutralized with concentrated hydrochloric acid. The neutralized product was extracted with ethyl acetate, and the extract was washed with saturated sodium chloride. The extract was dried over sodium sulfate, and the solvent was distilled off to give 1.6 g of 4-methoxyimino-5-methylthiochroman-6-carboxylic acid (Compound a-1) (yield 63%).

Preparation Example 2

1.6 Grams of 4-methoxyimino-5,8-dimethylthiochroman-6-carboxylic acid (Compound a-2) was obtained from 5.4 g of 5,8-dimethyl-6-bromothiochroman-4-one in the same manner as in Example 1 (yield 30%).

Preparation Example 3

(1) 3.0 Grams (11 mmol) of 5,8-dimethyl-6-bromothiochroman-4-one and 2.2 g (22 mmol.) of O-ethylhydroxylamine hydrochloride were refluxed under heat in a mixed solvent containing 10 ml of ethanol and 10 ml of pyridine For 30 minutes. The solvents were distilled off under reduced pressure, and then the residue was treated with 5% hydrochloric acid and extracted with ethyl acetate. The so-obtained solution was consecutively washed with 5% aqueous potassium carbonate and with saturated sodium chloride solution and dried over sodium sulfate. The solvent was distilled off to give 3.2 g of 4-ethoxyimino- 5,8-dimethyl-6-bromothiochroman (yield 92%).

(2) 1.1 Grams (46 mmol) of magnesium was dispersed in 10 ml of THF, and 2.2 g (20 mmol) of ethyl bromide was added dropwise under nitrogen. The resultant mixture was allowed to react for 10 minutes, and then a solution of 3.2 g (10 mmol) of the 4-ethoxyimino-5,8-dimethyl-6-bromothiochroman obtained in the above (1) in THF was gradually added at room temperature. The mixture was refluxed for 3 hours and then cooled to room temperature, and carbon dioxide gas was bubbled For 1 hour. 5% Hydrochloric acid was added to the reaction mixture, and the reaction mixture was extracted with ether. The resultant ether layer was extracted with 5% aqueous potassium carbonate, and the aqueous layer was neutralized with concentrated hydrochloric acid. The neutralized product was extracted with ethyl acetate, and the extract was washed with saturated sodium chloride solution. The extract was dried over sodium sulfate, and then the solvent was distilled off to give 1.6 g of 4-ethoxyimino-5,8-dimethylthiochroman-6-carboxylic acid (Compound a-3) (yield 57%).

Preparation Example 4

A reaction scheme is first shown for facile understanding of the subject reaction.

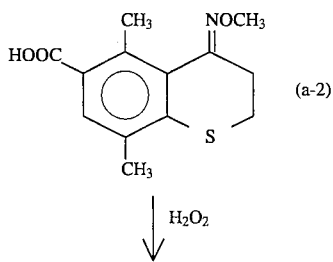

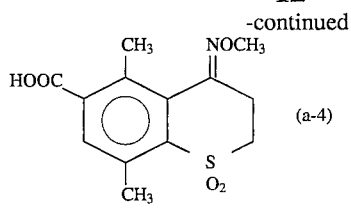

1.0 Gram (3.8 mmol) of the 4-methoxyimino-5,8 -dimethylthiochroman-6-carboxylic acid (Compound a-2) obtained in the above Preparation Example 2 was allowed to react with 1.3 g (12 mmol) of 30% hydrogen peroxide in 5 ml of acetic acid at 100° C. for 1 hour. Ethyl acetate was added to the reaction mixture, and the reaction mixture was washed with saturated sodium chloride solution and dried over sodium sulfate. The solvent was distilled off to give 1.1 g of 4 -methoxyimino-5,8-dimethylthiochroman-6-carboxylic acid-1,1 -dioxide (Compound a-4) (yield 97%).

Preparation Example 5

1.1. Grams of 4-ethoxyimino-5,8-dimethylthiochroman-6-carboxylic acid-1,1-dioxide (Compound a-5) was obtained from 1.0 g of 4-ethoxyimino-5,8-dimethylthiochroman- 6-carboxylic acid in the same manner as in Preparation Example 4 (yield 98%).

Preparation Example 6

4-Isopropoxyimino-5,8-dimethylthiochroman-6 -carboxylic acid (Compound a-6) was obtained from 5,8 -dimethyl-6-bromothiochroman-4-one in the same manner as in Preparation Example 1 with the yield being 34%.

Preparation Example 7

4-Isopropoxyimino-5,8-dimethylthiochroman-6 -carboxylic acid-1,1-dioxide (Compound a-7) was obtained from 4-isopropoxyimino-5,8-dimethyl thiochroman-6-carboxylic acid (Compound a-6) in the same manner as in Preparation Example 4 with the yield being 85%.

Preparation Example 8

4-Ethoxyimino-5-methylthiochroman-6-carboxylic acid-1,1-dioxide (Compound a-8) was obtained from 5-methyl-6-bromothiochroman-4-one in the same manner as in Preparation Examples 3 and 4 with the yield being 92%.

Table 1 shows the structures, amounts and yields of the compounds obtained in Preparation Examples 1 to 8.

TABLE 1

| Prep. Ex. No. | Starting material | Synthesized Compound No. | Structural formula | Amount (g) | Yield (%) |
|---|---|---|---|---|---|
| 1 | (Br, CH₃, C=O, S thiochromanone) | a-1 | (HOOC, CH₃, NOCH₃, S) | 1.6 | 59 |
| 2 | (Br, CH₃, CH₃, C=O, S) | a-2 | (HOOC, CH₃, CH₃, NOCH₃, S) | 1.6 | 30 |
| 3 | (Br, CH₃, CH₃, C=O, S) | a-3 | (HOOC, CH₃, CH₃, NOC₂H₅, S) | 1.6 | 52 |
| 4 | (HOOC, CH₃, CH₃, NOCH₃, S) (a-2) | a-4 | (HOOC, CH₃, CH₃, NOCH₃, S, O₂) | 1.1 | 97 |
| 5 | (HOOC, CH₃, CH₃, NOC₂H₅, S) (a-3) | a-5 | (HOOC, CH₃, CH₃, NOC₂H₅, S, O₂) | 1.1 | 98 |
| 6 | (Br, CH₃, CH₃, C=O, S) | a-6 | (HOOC, CH₃, CH₃, NOC₃H₇-i, S) | 1.3 | 34 |
| 7 | (HOOC, CH₃, CH₃, NOC₃H₇-i, S) (a-6) | a-7 | (HOOC, CH₃, CH₃, NOC₃H₇-i, S, O₂) | 0.6 | 85 |
| 8 | (Br, CH₃, C=O, S) | a-8 | (HO₂C, CH₃, NOC₂H₅, S, O₂) | 1.2 | 92 |

Table 2 shows the physical properties of the compounds obtained in Examples 1 to 8.

TABLE 2

| Preparation Example No. | Compound No. | NMR (δ, ppm) (deuterochloroform) | IR (cm$^{-1}$) |
|---|---|---|---|
| 1 | a-1 | 2.73(3H, s), 2.8–3.3(4H, m) 4.00(3H, s), 7.18(1H, s) 7.72(1H, d) | — |
| 2 | a-2 | 2.32(3H, s), 2.73(3H, s) 2.7–3.3(4H, m) 3.99(3H, s), 7.75(1H, s) | 2970, 1700, 1270 1060 |
| 3 | a-3 | 1.32(3H, t), 2.33(3H, s) 2.71(3H, s), 2.8–3.3(4H, m) 4.25(2H, q), 7.75(1H, s) | 2980, 2940, 1680 1280, 1260, 1050 |
| 4 | a-4 | 2.65(3H, s), 2.73(3H, s) 3.1–3.5(4H, m) 4.03(3H, s), 7.67(1H, s) | 3010, 2970, 1710 1320, 1130 |
| 5 | a-5 | 1.34(3M, t), 2.68(3H, s) 2.74(3H, s), 3.1–3.7(4H, m) 4.28(2H, q), 7.76(1H, s) | 2990, 2950, 1680 1310, 1120 |
| 6 | a-6 | 1.29(6H, d), 2.32(3H, s) 2.72(3H, s), 2.8–3.3(4H, m) 4.41(1H, m), 7.74(1H, s) | 3000, 1690, 1270 940 |
| 7 | a-7 | 1.31(6H, d), 2.63(3H, s) 2.71(3H, s), 3.3–3.4(4H, m) 4.46(1H, m), 7.65(1H, s) | 2980, 1715, 1320 1140, 995 |
| 8 | a-8 | 1.35(3H, t), 2.72(3H, s) 3.2–3.5(4H, m), 4.30(2H, q) 7.89(2H, s) | 3500–2900, 1720 1330, 1050 |

PREPARATION EXAMPLES OF PYRAZOLE DERIVATIVES

Preparation Example 9

A reaction scheme is first shown for facile understanding of the subject reaction.

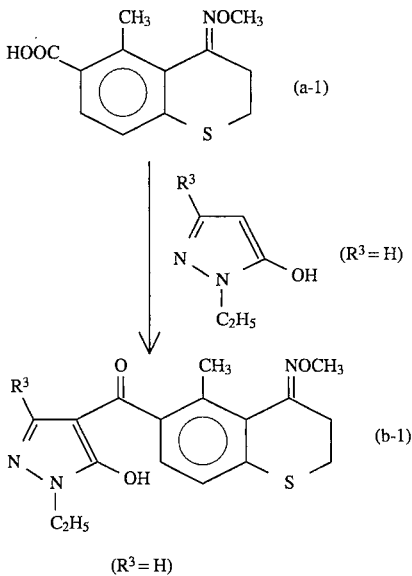

0.9 Gram (3.6 mmol) of the 4-methoxyimino-5-methylthiochroman-6-carboxylic acid (Compound a-1) obtained in Preparation Example 1 and 0.44 g (3.9 mmol) of 1-ethyl-5-hydroxypyrazole were dissolved in 5 ml of t-amyl alcohol, and 0.81 g (3.9 mmol) of DCC (dicyclohexylcarbodiimide) was added at room temperature. The mixture was stirred at room temperature for 2 hours, and 0.74 g (5.4 mmol) of potassium carbonate was added. The mixture was allowed to react at 90° C. for 8 hours. After the reaction, the solvent was distilled off, ethyl acetate was added, and the mixture was extracted with a 5% aqueous potassium carbonate. The aqueous layer was neutralized with concentrated hydrochloric acid, and then extracted with ethyl acetate. The resultant extract was washed with saturated sodium chloride solution, dried over sodium sulfate and concentrated to give 0.88 g of 4-methoxyimino-5-methyl-6-(1-ethyl-5-hydroxypyrazol-4-yl)carbonylthiochroman (Compound b-1) (yield 71%).

Preparation Example 10

4-Methoxyimino-5,8-dimethyl-6-(1-ethyl-5-hydroxypyrazol-4-yl)carbonylthiochroman (Compound b-2) was obtained from the above Compound a-2 in the same manner as in Example 9 with the yield being 67%.

Preparation Example 11

4-Methoxyimino-5,8-dimethyl-6-(1-ethyl-5-hydroxypyrazol-4-yl) carbonylthiochroman-1,1-dioxide (Compound b-3) was obtained from the above Compound a-4 in the same manner as in Example 9 with the yield being 81%.

Preparation Example 12

4-Ethoxyimino-5,8-dimethyl-6-(1-ethyl-5-hydroxypyrazol-4-yl)carbonylthiochroman (Compound b-4) was obtained from the above Compound a-3 in the same manner as in Example 9 with the yield being 68%.

Preparation Example 15

4-Ethoxyimino-5,8-dimethyl-6-(1-ethyl-5-hydroxypyrazol-4-yl)carbonylthiochroman-1,1-dioxide (Compound b-5) was obtained from the above Compound a-5 in the same manner as in Example 9 with the yield being 57%.

Preparation Example 14

A reaction scheme is first shown for facile understanding of the subject reaction.

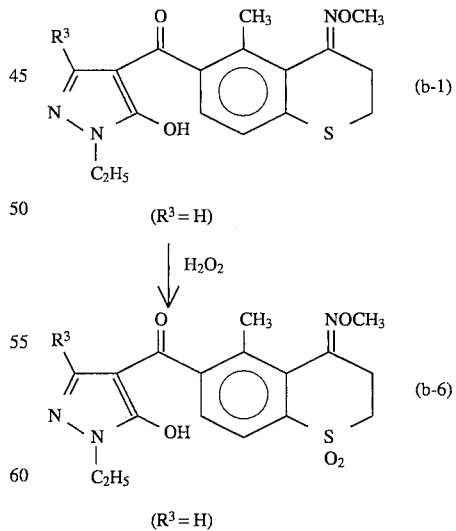

0.33 Gram (0.96 mmol) of the 4-methoxyimino-5-methyl-6-(1-ethyl-5-hydroxypyrazol-4-yl)carbonylthiochroman (Compound b-1) was allowed to react with 0.3 g (2.7 mmol) of 30% hydrogen peroxide in 3 ml of acetic acid at 100° C. for 1 hour. The reaction mixture was dissolved in ethyl acetate, washed with saturated sodium chloride solution, and dried over sodium sulfate. The solvent was distilled off to give 0.35 g of 4-methoxyimino-5-methyl-6-(1-ethyl-5-hydroxypyrazol-4-yl)carbonylthiochroman- 1,1-dioxide (Compound b-6) (yield 97%).

Preparation Example 15

4-Methoxyimino-5,8-dimethyl-6-(1-ethyl-5 -hydroxypyrazol-4-yl) carbonylthiochroman-1,1-dioxide (Compound b-3) was obtained from the above Compound b-2 in the same manner as in Preparation Example 14 with the yield being 97%.

Preparation Example 16

4-Ethoxyimino-5,8-dimethyl-6-(1-ethyl-5 -hydroxypyrazol-4-yl) carbonylthiochroman-1,1-dioxide (Compound b-5) was obtained from the above Compound b-4 in the same manner as in Preparation Example 14 with the yield being 98%.

Preparation Example 17

4-Isopropoxyimino-5,8-dimethyl-6-(1-ethyl-5 -hydroxypyrazol-4-yl) carbonylthiochroman-1,1-dioxide (Compound b-7) was obtained from the above Compound a-7 in the same manner as in Preparation Example 9 with the yield being 52%.

Preparation Example 18

4-Methoxyimino-5,8-dimethyl-6-(1,3-dimethyl-5 -hydroxypyrazol -4-yl) carbonylthiochroman-1,1-dioxide (Compound b-8) was obtained from the above Compound a-4 in the same manner as in Example 9 except that the 1-ethyl-5 -hydroxypyrazole in Preparation Example 9 was replaced with 1,3-dimethyl-5-hydroxypyrazole, with the yield being 70%.

Preparation Example 19

4-Methoxyimino-5,8-dimethyl-6-(1-methyl -5 -hydroxypyrazol-4-yl)carbonylthiochroman-1,1-dioxide (Compound b-9) was obtained from the above Compound a-4 in the same manner as in Example 9 except that the 1-ethyl-5 -hydroxypyrazole in Preparation Example 9 was replaced with 1-methyl-5-hydroxypyrazole, with the yield being 68%.

Preparation Example 20

4-Ethoxyimino-5-methyl-6-(1-ethyl-5 -hydroxypyrazol-4-yl) carbonylthiochroman-1,1-dioxide (Compound b-10) was obtained from the above Compound a-8 in the same manner as in Preparation Example 9 with the yield being 52%.

Tables 3 to 5 show the structures, amounts and yields of the compounds obtained in Preparation Examples 9 to 20.

TABLE 3

| Prep. Ex. No. | Starting material | Synthesized Compound No. | Structural formula | Amount (g) | Yield (%) |
|---|---|---|---|---|---|
| 9 | a-1 | b-1 | [structure with NOCH$_3$, pyrazole-N-C$_2$H$_5$, OH, S] | 0.88 | 71 |
| 10 | a-2 | b-2 | [structure with NOCH$_3$, CH$_3$, pyrazole-N-C$_2$H$_5$, OH, S, CH$_3$] | 0.83 | 67 |
| 11 | a-4 | b-3 | [structure with NOCH$_3$, CH$_3$, pyrazole-N-C$_2$H$_5$, OH, SO$_2$, CH$_3$] | 1.1 | 81 |
| 12 | a-3 | b-4 | [structure with NOC$_2$H$_5$, CH$_3$, pyrazole-N-C$_2$H$_5$, OH, S, CH$_3$] | 0.91 | 68 |

TABLE 4

| Prep. Ex. No. | Starting material | Synthesized Compound No. | Structural formula | Amount (g) | Yield (%) |
|---|---|---|---|---|---|
| 13 | a-5 | b-5 | [structure with $NOC_2H_5$, $C_2H_5$, $CH_3$, $CH_3$, $SO_2$] | 0.74 | 57 |
| 14 | b-1 | b-6 | [structure with $NOCH_3$, $C_2H_5$, $CH_3$, $SO_2$] | 0.35 | 97 |
| 15 | b-2 | b-3 | [structure with $NOCH_3$, $C_2H_5$, $CH_3$, $CH_3$, $SO_2$] (same as in Prep. Ex. 11) | 0.35 | 97 |
| 16 | b-4 | b-5 | [structure with $NOC_2H_5$, $C_2H_5$, $CH_3$, $CH_3$, $SO_2$] (same as in Prep. Ex. 13) | 0.35 | 98 |

TABLE 5

| Prep. Ex. No. | Starting material | Synthesized Compound No. | Structural formula | Amount (g) | Yield (%) |
|---|---|---|---|---|---|
| 17 | a-7 | b-7 | [structure with $NOC_3H_7\text{-}i$, $C_2H_5$, $CH_3$, $CH_3$, $SO_2$] | 0.56 | 52 |
| 18 | a-4 | b-8 | [structure with $CH_3$, $NOCH_3$, $CH_3$ (on N), $CH_3$, $CH_3$, $SO_2$] | 0.72 | 70 |

TABLE 5-continued

| Prep. Ex. No. | Starting material | Synthesized Compound No. | Structural formula | Amount (g) | Yield (%) |
|---|---|---|---|---|---|
| 19 | a-4 | b-9 | 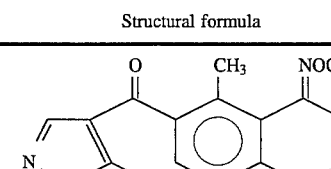 | 0.71 | 68 |
| 20 | a-8 | b-10 | 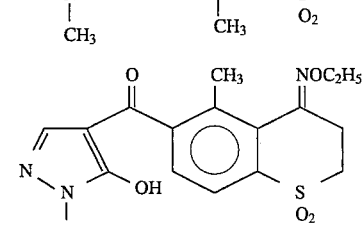 | 0.32 | 52 |

Table 6 shows the physical property values of the compounds obtained in Examples 6 to 11.

TABLE 6

| Prep. Ex. No. | Compound No. | NMR (δ, ppm) | IR (cm$^{-1}$) |
|---|---|---|---|
| 9 | b-1 | 1.46(3H, t), 2.58(3H, s), 2.6–3.3(4H, m) 4.00(3H, s), 4.06(2H, q), 6.97(1H, s) 7.29(1H, s), 7.2–7.5(2H, m), (deuterochloroform) | — |
| 10 | b-2 | 1.45(3H, t), 2.32(3H, s), 2.53 (3H, s) 2.8–3.3(4H, m), 3.98(3H, s), 4.07(2H, q) 7.19(1H, S), 7.42(1H, s), 8.17(1H, s) (deuterochloroform) | — |
| 11 | b-3 | 1.47(3H, t), 2.50(3H, s), 2.74(3H, s) 3.36(4H, m), 4.04(3H, s), 4.08(2H, q) 6.03(1H, s), 7.28(1H, s), 7.34(1H, s) (deuterochloroform) | 3010, 2970, 1740 1640, 1140, 1060 |
| 12 | b-4 | 1.31(3H, t), 1.47(3H, t), 2.32(3H, s) 2.51(3H, s), 2.8–3.3(4H, m), 4.06(2H, q) 4.22(2H, q), 6.04(1H, s), 7.18(1H, s) 7.35(1H, s) (deuterochloroform) | 3150, 2980, 2940 1740, 1620, 1240 1220, 1050 |
| 13 | b-5 | 1.33(3H, t), 1.46(3H, t), 2.49(3H, s) 2.74(3H, s), 3.37(4H, m), 4.10(2H, q) 4.28(2H, q), 6.60(1H, s), 7.27(1H, s) 7.34(1H, s) (deuterochloroform) | 3450, 3000, 1720 1630, 1130, 1050 |
| 14 | b-6 | 1.28(3H, t), 2.58(3H, s), 3.1–3.7(4H, m) 4.02(3H, s), 3.9–4.2(2H, m) 7.5–8.0(2H, m), 7.82(1H, s) (d6-DMSO) | 3250, 2920, 1730 1630, 1130, 1050 |
| 17 | b-7 | 1.31(3H, d), 1.46(3H, t), 2.48(3H, s) 2.74(3H, s), 3.2–3.5(4H, m) 4.08(2H, q), 7.25(1H, s), 7.34(1H, s) (deuterochloroform) | 3450, 3000, 1660 1640, 1130, 990 |
| 18 | b-8 | 1.67(3H, s), 2.40(3H, s), 2.70(3H, s) 3.2–3.7(4H, m), 3.59(3H, s) 4.02(3H, s), 4.95(1H, s), 7.28(1H, s) (d6-acetone) | 3450, 2950, 1740 1630, 1130, 1050 |
| 19 | b-9 | 2.43(3H, s), 2.70(3H, s), 3.2–3.7(4H, m), 3.67(3H, s) 4.01(3H, s), 5.08(1H, s), 7.35(1H, s) (d6-acetone) | 3430, 2940, 1710 1630, 1120, 1040 |
| 20 | b-10 | 1.35(3H, t), 1.47(3H, t), 2.58(3H, s) 3.2–3.5(4H, m), 4.08(2H, q) 4.30(2H, q), 7.31(1H, s), 7.74(2H, ABq) (deuterochloroform) | 3250, 3000, 1630 1120, 1050 |

HERBICIDE EXAMPLE

(1) Preparation of Herbicide

97 Parts by weight of talc (trade name: Zeaklite) as a carrier, 1.5 parts by weight of alkylarylsulfonic acid (trade name: Neoplex, supplied by Kao-Atlas K.K.) as a surfactant arid 1.5 parts by weight of a nonionic and anionic surfactant (trade name: Sorpol 800A, supplied by Toho Chemical Co., Ltd.) were uniformly pulverized and mixed to obtain a carrier for a wettable powder.

90 Parts by weight of the above carrier arid 10 parts by weight of one compound taken from Compounds of the present invention obtained in the above Preparation Examples (or 10 parts by weight of the following compound (a) or (b) as a comparative herbicide) were uniformly pulverized and mixed to obtain a herbicide.

The compounds (a) and (b) used as the comparative herbicides have the following structures.

Compound (a): Commercially available herbicide pyrazolate

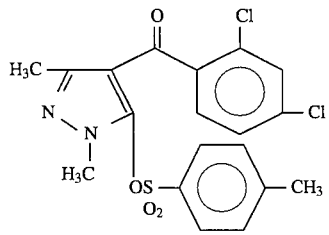

Compound (b):

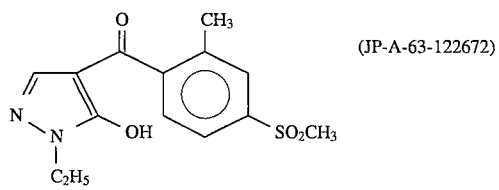

(JP-A-63-122672)

(2) Biological test (Foliar treatment test)

Seeds of weeds such as crabgrass, barnyardgrass, green foxtail, cocklebur, velvetleaf and slender amaranth and seeds of corn, wheat and barley were sown in 1/5,000 are Wagner pots filled with upland soil, and covered with upland soil. Then, the seeds were grown in a greenhouse, and when they grew to plants at one or two-leaved stage, a predetermined amount of the herbicide prepared in the above (1) was suspended in water and uniformly sprayed to foliar portions at a rate of 200 liter/10 are. Thereafter the plants were grown in the greenhouse, and 20 days after the treatment, the herbicide was determined for herbicidal efficacy and phytotoxicity to the crops. Table 7 shows the results.

The herbicidal efficacy and the phytotoxicity to the crops are shown on the basis of the following ratings.

| (Ratings) | Remaining plant weight/ non-treated ratio [%] |
| --- | --- |
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity | |
| – | 100 |
| ± | 95–99 |
| + | 90–94 |
| ++ | 80–89 |
| +++ | 0–79 |

The remaining plant weight/non-treated ratio was calculated by (remaining plant weight in treated area/remaining plant weight in non-treated area)×100.

TABLE 7

| Test Compound | Dosage [g(a.i.)are] | Herbicidal efficacy | | | | | | Phytotoxicity | | |
| --- | --- | --- | --- | --- | --- | --- | --- | --- | --- | --- |
| | | Crab-grass | Barnyard-glass | Green foxtail | Cockle-bur | Velvet leaf | Slender amaranth | Corn | Wheat | Barley |
| (a) | 12.5 | 0 | 0 | 0 | 0 | 0 | 1 | — | — | — |
| (b) | 3.2 | 0 | 0 | 0 | 3 | 3 | 2 | — | — | — |
| b-1 | 12.5 | 5 | 5 | 5 | 5 | 5 | 5 | — | — | — |
| | 3.2 | 5 | 5 | 5 | 4 | 5 | 4 | — | — | — |
| b-2 | 12.5 | 5 | 5 | 5 | 5 | 5 | 5 | — | — | — |
| | 3.2 | 5 | 5 | 5 | 5 | 5 | 5 | — | — | — |
| b-3 | 12.5 | 5 | 5 | 5 | 5 | 5 | 5 | — | — | — |
| | 3.2 | 5 | 5 | 5 | 5 | 5 | 5 | — | — | — |
| b-4 | 12.5 | 5 | 5 | 5 | 5 | 5 | 5 | — | — | — |
| | 3.2 | 5 | 5 | 5 | 5 | 5 | 5 | — | — | — |
| b-5 | 12.5 | 5 | 5 | 5 | 5 | 5 | 5 | — | — | — |
| | 3.2 | 5 | 5 | 5 | 5 | 5 | 5 | — | — | — |
| b-6 | 12.5 | 5 | 5 | 5 | 5 | 5 | 5 | — | — | — |
| | 3.2 | 5 | 5 | 5 | 5 | 5 | 5 | — | — | — |
| b-7 | 12.5 | 5 | 5 | 5 | 5 | 5 | 5 | — | — | — |
| | 3.2 | 5 | 5 | 5 | 5 | 5 | 5 | — | — | — |
| b-8 | 12.5 | 5 | 5 | 5 | 5 | 5 | 5 | — | — | — |
| | 3.2 | 5 | 5 | 5 | 5 | 5 | 5 | — | — | — |
| b-9 | 12.5 | 5 | 5 | 5 | 5 | 5 | 5 | — | — | — |

TABLE 7-continued

| Test Compound | Dosage [g(a.i.)are] | Herbicidal efficacy | | | | | | Phytotoxicity | | |
|---|---|---|---|---|---|---|---|---|---|---|
| | | Crab-grass | Barnyard-glass | Green foxtail | Cockle-bur | Velvet leaf | Slender amaranth | Corn | Wheat | Barley |
| | 3.2 | 5 | 5 | 5 | 5 | 5 | 5 | — | — | — |
| b-10 | 12.5 | 5 | 5 | 5 | 5 | 5 | 5 | — | — | — |
| | 3.2 | 5 | 5 | 5 | 5 | 5 | 5 | — | — | — | a.i. = abbreviation for active ingredient (3) Biological test (Soil treatment test)

Seeds of weeds such as crabgrass, barnyardgrass, green foxtail, cocklebur, velvetleaf and slender amaranth and seeds of corn, wheat and barley were sown in 1/5,000 are Wagner pots filled with upland soil, and covered with upland soil. Then, a predetermined amount of the herbicide prepared in the above (1) was suspended in water and uniformly sprayed onto the soil surface. Thereafter the seeds were grown in the greenhouse, and 20 days after the treatment, the herbicide was determined for herbicidal efficacy and phytotoxicity to the crops. Table 8 shows the results.

TABLE 8

| Test Compound | Dosage [g(a.i.)are] | Herbicidal efficacy | | | | | | Phytotoxicity | | |
|---|---|---|---|---|---|---|---|---|---|---|
| | | Crab-grass | Barnyard-glass | Green foxtail | Cockle-bur | Velvet leaf | Slender amaranth | Corn | Wheat | Barley |
| (a) | 12.5 | 1 | 1 | 0 | 0 | 1 | 1 | — | — | — |
| (b) | 3.2 | 1 | 1 | 1 | 2 | 0 | 0 | — | — | — |
| b-3 | 12.5 | 5 | 5 | 5 | 5 | 5 | 5 | — | — | — |
| | 3.2 | 5 | 4 | 5 | 4 | 5 | 5 | — | — | — |
| b-5 | 12.5 | 5 | 5 | 5 | 5 | 5 | 5 | — | — | — |
| | 3.2 | 5 | 5 | 5 | 5 | 5 | 5 | — | — | — |
| b-6 | 12.5 | 5 | 5 | 5 | 5 | 5 | 5 | — | — | — |
| | 3.2 | 5 | 5 | 5 | 5 | 5 | 5 | — | — | — |
| b-7 | 12.5 | 5 | 5 | 5 | 5 | 5 | 5 | — | — | — |
| | 3.2 | 5 | 5 | 5 | 5 | 5 | 5 | — | — | — |
| b-8 | 12.5 | 5 | 5 | 5 | 5 | 5 | 5 | — | — | — |
| | 3.2 | 5 | 5 | 5 | 5 | 5 | 5 | — | — | — |
| b-9 | 12.5 | 5 | 5 | 5 | 5 | 5 | 5 | — | — | — |
| | 3.2 | 5 | 5 | 5 | 5 | 5 | 5 | — | — | — |
| b-10 | 12.5 | 5 | 5 | 5 | 5 | 5 | 5 | — | — | — |
| | 3.2 | 5 | 5 | 5 | 5 | 5 | 5 | — | — | — | a.i. = abbreviation for active ingredient

Tables 7 and 8 clearly show that the pyrazole derivative-containing herbicide of the present invention shows no phytotoxicity to corn, wheat and barley and exhibits an excellent weed control effect on grasses (crabgngrass, barnyardgrass and green foxtail) and broad-leaved weeds (cocklebur, velvetleaf and slender amaranth) at a low dosage. In contrast, the herbicide containing the known pyrazole derivative (a) and the herbicide containing the known pyrazole derivative (b) do not perform any sufficient herbicidal efficacy.

As specified above, according to the present invention, there have been provided the novel pyrazole derivatives or salts thereof which show high selectivity to corn, wheat and barley and which are capable of controlling grasses and broad-leaved weeds at a low dosage; a herbicide containing one of the above novel pyrazole derivatives and/or salts thereof as am active ingredient; and novel intermediate compounds suitable for the production of the above novel pyrazole derivatives and/or salts thereof.

We claim:

1. A pyrazole derivative of the formula (I),

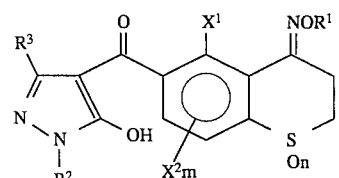

(wherein $R^1$ is a $C_1$–$C_6$ alkyl group, each of $R^2$, $X^1$ and $X^2$ is independently a $C_1$–$C_4$ alkyl group, $R^3$ is hydrogen or a $C_1$–$C_4$ alkyl group, m is an integer of 0 or 1, and n is an integer of 0, 1 or 2.) or a salt thereof.

2. A pyrazole derivative or a salt thereof according to claim 1, wherein $R^1$ is a $C_1$–$C_4$ alkyl group.

3. A pyrazole derivative or a salt thereof according to claim 2, wherein $R^1$ is methyl, ethyl or i-propyl.

4. A pyrazole derivative or a salt thereof according to claim 1, wherein $R^2$ is methyl or ethyl.

5. A pyrazole derivative or a salt thereof according to claim 1, wherein the alkyl group included in $R^3$ is hydrogen.

6. A pyrazole derivative or a salt thereof according to claim 1, wherein $X^1$ is methyl.

7. A pyrazole derivative or a salt thereof according to claim 1, wherein $X^2$ is methyl.

8. A pyrazole derivative or a salt thereof according to claim 1, wherein m is 0.

9. A pyrazole derivative or a salt thereof according to claim 1, wherein $X^2$ is substituted on the 8-position when m is 1.

10. A pyrazole derivative or a salt thereof according to claim 1, wherein n is 2.

11. A pyrazole derivative or a salt thereof according to claim 1, which is a 4-methoxyimino-5-methyl-6-(1-ethyl-5-hydroxypyrazol-4-yl)carbonylthiochroman.

12. A pyrazole derivative or a salt thereof according to claim 1, which is a 4-methoxyimino-5,8-dimethyl-6-(1-ethyl-5-hydroxypyrazol-4-yl)carbonylthiochroman.

13. A pyrazole derivative or a salt thereof according to claim 1, which is a 4-methoxyimino-5,8-dimethyl-6-(1-ethyl-5-hydroxypyrazol-4-yl)carbonylthiochroman-1,1-dioxide.

14. A pyrazole derivative or a salt thereof according to claim 1, which is a 4-ethoxyimino-5,8-dimethyl-6-(1-ethyl-5-hydroxypyrazol-4-yl)carbonylthiochroman.

15. A pyrazole derivative or a salt thereof according to claim 1, which is a 4-ethoxyimino-5,8-methyl-6-(1-ethyl-5-hydroxypyrazol-4-yl)carbonylthiochroman-1,1-dioxide.

16. A pyrazole derivative or a salt thereof according to claim 1, which is a 4-methoxyimino-5-methyl-6-(1-ethyl-5-hydroxypyrazol-4-yl)carbonylthiochroman-1,1-dioxide.

17. A pyrazole derivative or a salt thereof according to claim 1, which is a 4-isopropoxyimino-5,8-dimethyl-6-(1-ethyl-5-hydroxypyrazol-4-yl)carbonylthiochroman-1,1-dioxide.

18. A pyrazole derivative or a salt thereof according to claim 1, which is a 4-methoxyimino-5,8-dimethyl-6-(1,3-dimethyl-5-hydroxypyrazol-4-yl)carbonylthiochroman-1,1-dioxide.

19. A pyrazole derivative or a salt thereof according to claim 1, which is a 4-methoxyimino-5,8-dimethyl-6-(1-methyl-5-hydroxypyrazol-4-yl)carbonylthiochroman-1,1-dioxide.

20. A pyrazole derivative or a salt thereof according to claim 1, which is a 4-ethoxyimino-5-methyl-6-(1-ethyl-5-hydroxypyrazol-4-yl)carbonylthiochroman-1,1-dioxide.

21. A herbicide containing, (i) a herbicidal carrier and (ii) as an active ingredient, a pyrazole derivative of the formula (I).

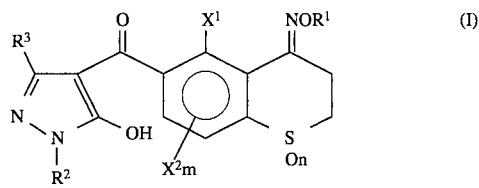

(wherein $R^1$ is a $C_1$–$C_6$ alkyl group, each of $R^2$, $X^1$ and $X^2$ is independently a $C_1$–$C_4$ alkyl group, $R^3$ is hydrogen or a $C_1$–$C_4$ alkyl group, m is an integer of 0 or 1, and n is an integer of 0, 1 or 2) or a salt thereof.

* * * * *